United States Patent [19]

Newman

[11] Patent Number: 5,106,751
[45] Date of Patent: * Apr. 21, 1992

[54] APPARATUS FOR SUPPORTING A BIOCHEMICAL SENSOR RESPONSIVE TO BUBBLES

[75] Inventor: Arnold L. Newman, Kensington, Md.

[73] Assignee: Biotronic Systems Corporation, Rockville, Md.

[*] Notice: The portion of the term of this patent subsequent to Oct. 15, 2008 has been disclaimed.

[21] Appl. No.: 350,222

[22] Filed: May 11, 1989

Related U.S. Application Data

[63] Continuation-in-part of Ser. No. 244,677, Sep. 15, 1988.

[51] Int. Cl.$^5$ .................. C12M 1/42; C12M 1/40; C12M 1/34
[52] U.S. Cl. .................. 435/288; 435/291; 435/807; 435/817; 435/808; 204/403
[58] Field of Search ............ 435/4, 7, 173, 180, 435/181, 288, 291, 807, 817, 808, 7.1–7.95; 436/518, 528, 531, 532, 164, 172, 805, 806, 807; 422/68, 69, 80, 90, 91, 82.01–82.11; 324/71.1, 71.5, 691, 692; 204/400, 403

[56] References Cited

U.S. PATENT DOCUMENTS

| | | | |
|---|---|---|---|
| 4,392,933 | 7/1983 | Nakamura et al. | 435/817 |
| 4,562,157 | 12/1985 | Lowe et al. | 435/291 |
| 4,728,882 | 3/1988 | Stanbro et al. | 204/400 |
| 4,789,804 | 12/1988 | Karube et al. | 435/4 |
| 4,844,869 | 7/1989 | Glass | 435/808 |

OTHER PUBLICATIONS

Schmid "Trends in Biosensors", Biofutur (1988) pp. 37–41.

Primary Examiner—David L. Lacey
Assistant Examiner—William H. Beisner
Attorney, Agent, or Firm—Kerkam, Stowell, Kondracki & Clarke

[57] ABSTRACT

A biochemical sensor includes a material that nucleates as bubbles on the surface of an electrical conductor, optical fiber, or acoustic medium. The nucleating bubbles respectively change the conductivity, refraction, or propagation of such surfaces according to the concentration of the analyte in a solution over the sensor.

14 Claims, 3 Drawing Sheets

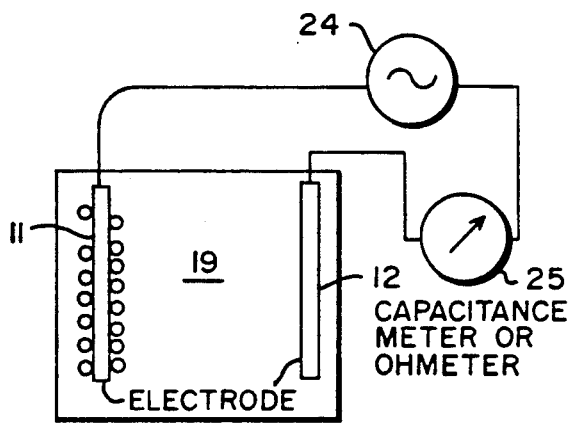
FIG. 2
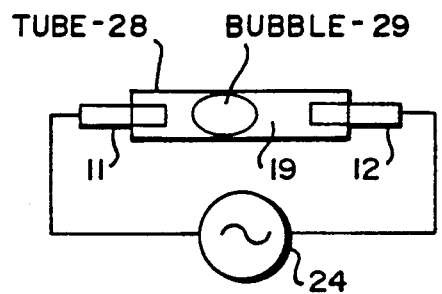
FIG. 4
FIG. 7
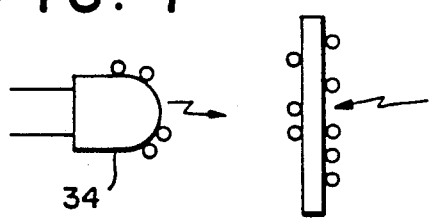
FIG. 9
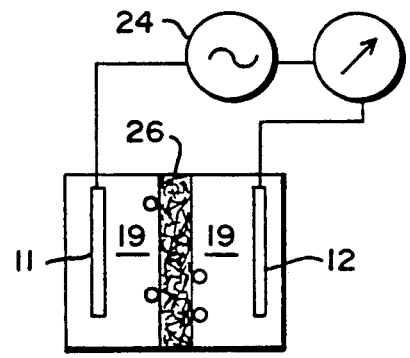
FIG. 3
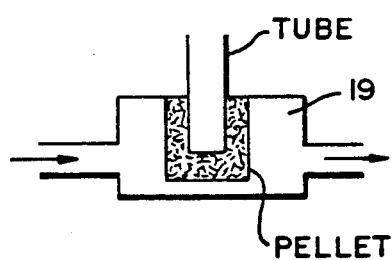
FIG. 6
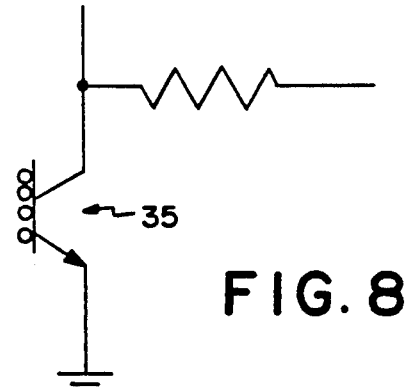
FIG. 8
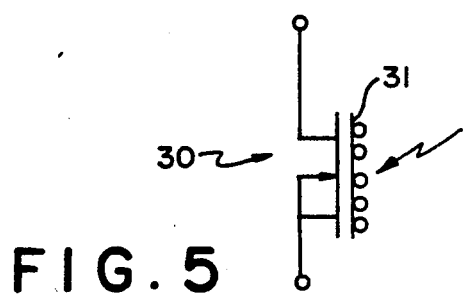
FIG. 5

APPARATUS FOR SUPPORTING A BIOCHEMICAL SENSOR RESPONSIVE TO BUBBLES

This is a continuation-in-part application of Ser. No. 244,677, for BIOCHEMICAL SENSOR RESPONSIVE TO BUBBLES, filed Sept. 15, 1988.

FIELD OF THE INVENTION

This invention relates to an apparatus for supporting a biochemical sensor, and more specifically relates to embodiments of the apparatus for supporting a sensor using a combination of an enzyme and a substrate for detecting the presence of analytes in a solution.

BACKGROUND OF THE INVENTION

Capacitive affinity sensors have been used to measure the concentration of an analyte by detecting a change in capacitance as an analyte molecule moves in or out of an electric field between two electrodes of the sensor in a direct mode, for instance. The moving analyte molecules change the dielectric properties of a biochemically active layer between the two electrodes. The displacement of the solvent molecules by the analyte molecules reduces the measured capacitance between the two electrodes. The capacitance between the two electrodes changes in relation to the concentration of the analyte being measured by such a sensor, for instance. In an indirect mode, large detector molecules, such as antibodies, move in or out of the electric field between the two electrodes to change the dielectric properties of the biochemically active layer. Such capacitive affinity sensors, however, have a sensitivity limited by the amount of water displaced from the sensor surface by biomolecules.

Such sensors are described in the background of parent U.S. Pat. application Ser. No. 244,677; for BIOCHEMICAL SENSOR RESPONSIVE TO BUBBLES filed Sept. 15, 1988; to Arnold L. Newman; and assigned to the same assignee as the present invention. The background of U.S. Pat. application Ser. No. 244,677 is incorporated by reference.

U.S. Pat. No. 4,562,157 for a DIAGNOSTIC DEVICE INCORPORATING A B LIGAND; patented Dec. 31, 1985; to Christopher R. Lowe et al.; concerns a technique for covalently binding a biochemical group to a sensor surface through a mask, making possible "printed circuits for proteins". The patent states at Column 9, line 65-21, that the device of the invention need not be based on an FET. Other sensors can include transistor semiconductors, electrodes, crystals, opto-electronic devices, and fiber optic devices, for example.

FIG. 1 is from U.S. Pat. application Ser. No. 244,677 and illustrates biochemical activity of a capacitive sensor 10, which is responsive to bubbles. APS (3-aminopropyltriethoxy silane) 20 covers a layer of silicone rubber 18. APS 20 covalently binds and immobilizes a layer of an enzyme 21 to the silicone layer. APS is not necessary when the enzyme 21 is immobilized by adsorption onto the silicone layer 18. These immobilized enzyme molecules remain attached and stationary in the presence of any other biochemistry. The thickness of the layer of enzyme 20 is actually very small compared to the irregularities in the surface of the silicone rubber 18, but for clarity the thickness of the layer of enzyme 20 is exaggerated in FIG. 1. A substrate 22 to the enzyme 21 is added to the aqueous environment 19 covering the sensor surface 10. The substrate 22, in the presence of the enzyme 21, is transformed into a volatile material, for instance. The silicone rubber 18 is a surface on which the volatile material is capable of coming out of solution into the gas phase. Accordingly, bubbles 23 nucleate on the sensor surface.

The presence of nucleated bubbles at the sensor surface drastically alters the dielectric properties measured by the sensor compared to that measured in an absence of nucleated bubbles at the sensor surface. The gas bubbles 23 on the sensor surface displace molecules of the aqueous environment 19 from the sensor surface. As a result, there is a phase change at the sensor surface and within the components of the dielectric material. Specifically, liquid molecules comprising the aqueous environment 19 over the silicone rubber 18 are displaced by gas bubbles 23 when the bubbles nucleate. The gas bubbles 23 have a dielectric constant of 1-3 and the aqueous environment 19, comprising phosphate buffered saline (PBS), has a dielectric constant of over 78. This displacement of water by gas bubbles within the dielectric material drastically changes the dielectric properties of that material and thus the capacitance between the two electrodes 11 and 12.

Further details concerning the biochemistry of the capacitive sensor 10 are described in U.S. Pat. application Ser. No. 244,677; which is incorporated by reference.

BRIEF DESCRIPTION OF THE FIGURES

FIG. 2 shows an electrical embodiment having two electrodes.

FIG. 3 shows an electrical embodiment having two compartments separated by a filter.

FIG. 4 shows an electrical embodiment having two electrodes attached to a tube.

FIG. 5 shows an electrical embodiment comprising an FET transistor.

FIG. 6 shows an electrical embodiment comprising a sintered pellet.

FIG. 7 shows an optical embodiment comprising an LED.

FIG. 8 shows an opto-electronic embodiment comprising a switching device.

FIG. 9 shows an optical embodiment comprising a photo-detecting diode.

SUMMARY OF THE INVENTION

The invention concerns an apparatus for responding to an analyte. The apparatus comprises a device for conducting energy at a first level and having a surface, and a means comprising biochemistry for producing volatile molecules near the surface of the device according to the presence of an analyte. The volatile material comprises a means for nucleating bubbles near the surface of the device. The device also comprises a means for transmitting the energy at a second level in response to bubbles that nucleate on the surface of the device.

In different embodiments, the device comprises an electrical conductor, optical fiber, or acoustic waveguide. The conductivity, refraction, or propagation, respectively, changes from the first to the second level according to the presence of the analyte.

DETAILED DESCRIPTION OF THE INVENTION

FIGS. 2-14 illustrate different embodiments of an apparatus comprising a surface for supporting a biochemical sensor responsive to bubbles, as described in U.S. Pat. application Ser. No. 244,677, for instance. Specifically, an enzyme and a substrate at the surface and in a solution chemically produce a volatile material. The volatile material changes phase and nucleates bubbles. The nucleated bubbles form a gas bubble at the sensor surface. The gas bubble displaces a large volume of solution from adjacent the sensor surface, which drastically changes the transmission of energy on that surface from a first level to a second level.

Figure 1:
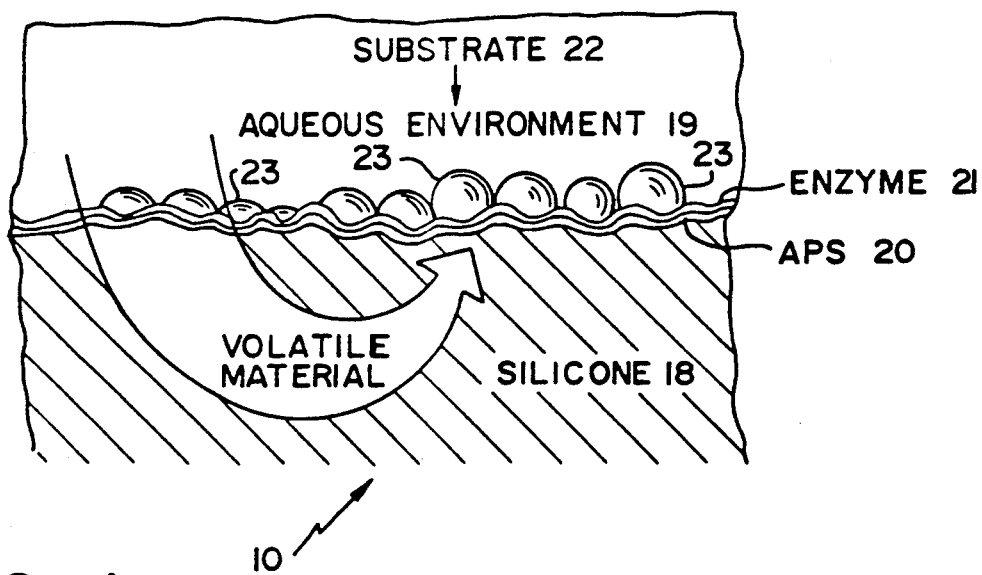
FIG. 1 illustrates biochemical activity of a sensor responsive to bubbles.

FIG. 2 shows an electrical embodiment of this invention. A capacitor has a bubble forming electrode 11 and a counter electrode 12. The bubble forming electrode 11 comprises a sensor surface on which bubbles nucleate as described concerning FIG. 1. The bubble forming electrode 11 transmits electrical energy from an electrical source 24, such as a sine wave voltage generator, at a relatively constant average energy level. Thus, the electrode 11 serves as an energy providing means and the electrode 12 serves as a reception means positioned to receive energy from the electrode 11. The electrode 11 has an outer surface where electrical conductivity occurs at a first level. An aqueous environment comprising an electrolyte solution 19 covers the surface of the electrode 11 and enhances conductivity at the surface of the electrode 11. An enzyme/substrate combination nucleates bubbles on the surface of the electrode 11 in response to the concentration of an analyte in the electrolyte solution 19 covering the electrode 11. Bubbles nucleate on the surface of the electrode 11 and displace molecules of the electrolyte solution 19 from the electrode surface. A resulting decrease in the area of the surface of the electrode 11 that interfaces with the electrolyte solution causes an increase in electrode impedance. Thus, capacitance decreases and resistance increases as more bubbles nucleate. This displacement of solution molecules directly affects the ability of the electrode 11 to transmit electrical energy, and quickly changes that energy from a first level to a second level, as measured by a capacitance meter or ohmeter 25.

In an embodiment comprising a single electrode having this chemistry and a counter electrode, electrode resistance increases as more bubbles nucleate. As capacitance decreases, resistance increases. Capacitive impedance increases according to $Z_c = 1/jwC$, where $Z_c$ is capacitive impedance, j is imaginary, w is freguency, and C is capacitance. The resistive term of the impedance is represented by a real component. However, the imaginary component, real component or phasor sum of these two components of impedance can be examined to determine the change in energy transmission from a first level to a second level.

FIG. 3 shows another electrical embodiment of this invention. A filter 26 separates a container 27 into two compartments that hold an electrolyte solution 19. In each compartment is an electrode 11 and 12. The filter 26 comprises a sensor surface on which bubbles nucleate as described concerning FIG. 1. The filter 26 transmits electrical energy from an electrical source, such as a DC and AC voltage source 24, at a first energy level. The filter 26 comprises a dielectric material and has a surface where electrical conductivity occurs at the first level. The surface of this filter 26 includes the surfaces of all fibers comprising a filter and the surfaces that define all pores of a filter, for instance. An electrolyte solution 19 at the surface of the filter 26 enhances conductivity through the filter 26 and between the two compartments of electrolyte solution. An enzyme/substrate combination causes molecules of a material to be produced, which nucleate as bubbles on the surface of the filter 26 in response to the concentration of an analyte in the electrolyte solution on both sides of the filter 26. Bubbles nucleate on the surface of the filter 26 and displace molecules of the electrolyte solution 19 from the filter surface, decreasing the total amount of conductive cross-section through the filter 26. A resulting decrease in the area of the filter 26 that interfaces with the electrolyte solution 19 causes an increase in filter impedance. Thus, capacitance decreases and resistance increases as more bubbles nucleate. This displacement of solution molecules directly affects the ability of the filter 26 to transmit electrical energy, and quickly changes that energy from a first level to a second level.

FIG. 4 shows another electrical embodiment of this invention. A thin tube 28 has a pair of electrodes 11 and 12. The inner surface of the thin tube 28 comprises a sensor surface on which bubbles nucleate as described concerning FIG. 1. An electrical source 24, such as a sine wave voltage generator, transmits electrical energy at a relatively constant energy level. An electrolyte solution 19 fills the tube 28 between the two electrodes 11 and 12 and conductivity occurs at a first level between the two electrodes 11 and 12. An enzyme/substrate combination on the inner surface of the tube 28 nucleates bubbles in response to the concentration of an analyte in the electrolyte solution. Bubbles nucleate on the inner surface of the tube 28, forming a large bubble 29 and displace molecules of the electrolyte solution 19 from between the two electrodes 11 and 12. A resulting decrease in the volume of electrolyte solution 19 that interfaces with the electrodes 11 and 12 causes an increase in impedance between the electrodes. Thus, capacitance decreases and resistance increases as more bubbles nucleate. This displacement of solution molecules directly affects the ability of the electrolyte to transmit electrical energy between the pair of electrodes 11 and 12 and quickly changes that energy from a first level to a second level.

FIG. 5 shows another electrical embodiment of this invention. A solid state electronic device, such as an FET transistor 30, has a bubble forming gate 31. The bubble forming gate comprises a sensor surface on which bubbles nucleate as described concerning FIG. 1. The gate 31 transmits electrical energy from an electrical source, such as a sine wave voltage generator (not shown), at a first energy level. The gate 31 has an outer surface where electrical conductivity occurs at that first level. An electrolyte solution (not shown) covers the surface of the gate 31 and enhances conductivity at the surface of the gate 31. An enzyme/substrate combination causes molecules of a material to be produced, which nucleate as bubbles on the surface of the gate 31 in response to the concentration of an analyte in the electrolyte solution covering the gate 31. Bubbles nucleate on the surface of the gate 31 and displace molecules of the electrolyte solution from the gate surface. A resulting decrease in the area of the gate 31 that interfaces with the electrolyte causes changes in the dielectric properties of the gate 31. Thus, electrical characteristics of the transistor 30 change as more bubbles nucleate. This displacement of electrolyte solution molecules directly affects the ability of the gate 31 to transmit electrical energy, and quickly changes that energy from a first level to a second level.

FIG. 6 shows another electrical embodiment of the invention. A sintered tantalum cup-shaped pellet 32 comprises a surface on which bubbles nucleate as described concerning FIG. 1. Sintered tantalum pellets are described in U.S. Pat. No. 4,769,121 to Arnold L. Newman for SINTERED PELLET WITH BIOCHEMICALLY ACTIVE LAYER, the specification of which is incorporated by reference. The pellet 32 comprises an electrode that transmits electrical energy at a first level from a source (not shown) through a solution covering the pellet 32 to a counter electrode (not shown) located elsewhere in the solution. A test substance enters the pellet 32 through a tube 33. An electrolyte solution 19 at the surface of the pellet 32 enhances the electrical properties, such as capacitance and resistance, of the pellet 32. An enzyme/substrate combination causes molecules of a material to be produced, which nucleate as bubbles on the surface of the pellet 32 in response to the concentration of an analyte in the solution 19. Bubbles nucleate on the surface of the pellet 32 and displace molecules of the solution from the pellet 32 surface. A resulting decrease in the area of the pellet 32 that interfaces with the electrolyte solution 19 causes an increase in pellet resistance. Thus, resistance increases as more bubbles nucleate. This displacement of solution molecules directly affects the ability of the pellet 32 to transmit electrical energy, and quickly changes that energy from a first level to a second level.

The electrical embodiments of FIGS. 2 to 6 can comprise an electrode of tantalum foil laminated to a plastic backing, for instance. Such an electrode can be manufactured inexpensively and could be disposable. The electrical embodiments of FIGS. 2 to 6 can comprise pairs of bubble nucleating electrodes.

FIG. 7 shows an optical embodiment of this invention. An optical source 34, such as a light emitting diode (LED), transmits optical energy at a first energy level to a photodetecting diode of FIG. 9, for instance. The optical source 34 has an outer surface on which bubbles nucleate as described concerning FIG. 1. A solution (not shown) containing an analyte covers the optical source 34 and light transmitted by the optical source 34 is attenuated by the solution at a corresponding first level. An enzyme/substrate combination causes molecules of a material to be produced, which nucleate as bubbles on the surface of the optical source 34 in response to the concentration of an analyte in the solution covering the optical source 34. Bubbles nucleate on the surface of the optical source 34 and displace molecules of the analyte solution from the optical source surface. A resulting decrease in the area of the optical source 34 that interfaces with the solution causes a change in light transmission. Thus, light intensity increases as more bubbles nucleate. This displacement of solution molecules directly affects refraction of light at the surface of the optical source 34, and quickly changes the intensity of light of the optical source 34 from the first level to a second level.

FIG. 8 shows an opto-electronic embodiment of this invention. A opto-electronic device 35, such as a photodetector, for instance, transmits electrical energy from an electrical source (not shown) at a first energy level. The opto-electronic device 35 has an outer surface on which bubbles nucleate as described concerning FIG. 1. A solution (not shown) covers the opto-electronic device, which is responsive to relatively constant light transmitted toward the surface of the opto-electronic device 35. The surface comprises a material having an electrical conductivity that is determined by the amount of light to which the material is exposed. An enzyme/substrate combination causes molecules of a material to be produced, which nucleate as bubbles on that surface in response to the concentration of an analyte in the solution covering the opto-electronic device. Bubbles nucleate on the surface of the opto-electronic device 35 and displace molecules of the solution from the opto-electronic device surface. A resulting decrease in the area of the opto-electronic device 35 that interfaces with the solution causes a change in the amount of light that reaches the surface of the device. Thus, light intensity changes at the surface and electrical conductivity of the opto-electronic device 35 changes as more bubbles nucleate. This displacement of solution molecules directly affects the ability of the opto-electronic device 35 to transmit electrical energy, and quickly changes that energy from a first level to a second level.

FIG. 9 shows another optical embodiment of this invention. An optical source, such as a light emitting diode (LED) of FIG. 7, transmits optical energy at a relatively constant energy level through an optical fiber 36 to a photodetecting diode of FIG. 8, for instance. The optical fiber 36 has an outer surface on which bubbles nucleate as described concerning FIG. 1. A solution covers the optical fiber 36 such that light transmitted in the optical fiber 36 is transmitted at a corresponding first level. An enzyme/substrate combination causes molecules of a material to be produced, which nucleate as bubbles on the surface of the optical fiber 36 in response to the concentration of an analyte in the solution covering the optical fiber 36. Bubbles nucleate on the surface of the optical fiber 36 and displace molecules of the analyte solution from the optical fiber surface. A resulting decrease in the area of the optical fiber 36 that interfaces with the solution causes a change in light refraction. Thus, light intensity changes as more bubbles nucleate. This displacement of solution molecules directly affects refraction of light at the surface of the optical fiber 36, which changes the intensity of light in the optical fiber from the first level to a second level.

Figure 10:
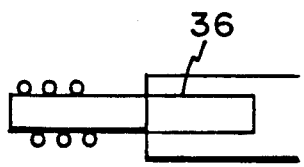
FIG. 10 shows a bio-optical embodiment including a fluorescent species.

FIG. 10 shows a bio-optical embodiment of this invention. An optical fiber 36 transmits optical energy, such as a light, from an optical source 34 of FIG. 7 at a first wavelength. The optical fiber 36 has an outer surface on which bubbles nucleate as described in FIG. 1. A solution (not shown) covers the optical fiber 36 such that light is excited in the optical fiber 36 at a first wavelength. A fluorescent species of an enzyme/substrate combination causes molecules of a material to be produced, which nucleate as bubbles on the surface of the optical fiber 36 in response to the concentration of an analyte in the solution covering the optical fiber. Bubbles nucleate on the surface of the optical fiber 36 and displace molecules of the solution from the optical fiber surface. This displacement of solution molecules directly affects the fluorescence of the species. Nucleating bubbles interfere with evanescent wave coupling of the fluorescent species and quickly changes the amount of light that couples into the optical fiber. Thus, light energy transmitted by the optical fiber changes from the first level to a second level. Thus, light wavelength changes as more bubbles nucleate.

Figure 11:
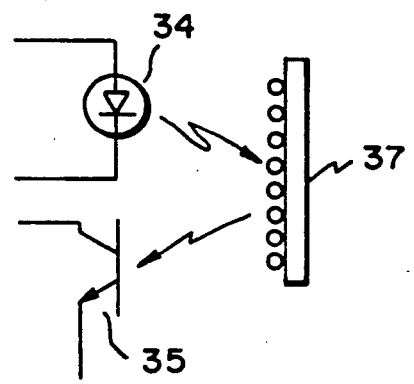
FIG. 11 shows an optical embodiment including a reflector.

FIG. 11 shows another optical embodiment of this invention. An optical source 34 such as a light emitting diode produces optical energy at a relatively constant energy level. Light from the optical source 34 reaches a mirror 37 and is reflected to an optical detector 35 comprising a photo-transistor, for instance. The mirror has a surface exposed to a solution (not shown) containing an analyte. Light transmitted from the optical source 34 is attentuated by the solution at a corresponding first level. An enzyme/substrate causes molecules of a material to be produced, which on the surface of the mirror 37 nucleate as bubbles on the surface in response to the concentration of an analyte in the solution covering the mirror 37. Bubbles nucleate on the surface of the mirror 37 and displace molecules of the solution from the mirror surface. A resulting decrease in the area of the mirror 37 that interfaces with the solution causes a change in reflected light. This displacement of solution molecules directly affects attenuation of light at the surface of the mirror 37, which changes the intensity of light reflected by the mirror 37 from the first level to a second level. Thus, the amount of reflected light intensity changes as more bubbles nucleate.

Figure 12:
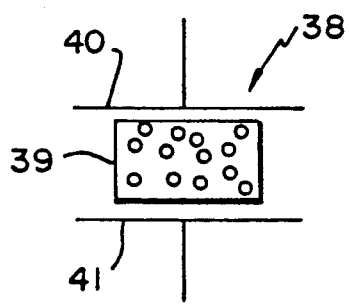
FIG. 12 shows an acoustic embodiment comprising a piezoelectric device.

FIG. 12 shows an acoustic embodiment of this invention. A sound source 38, such as a piezoelectric device, produces acoustic energy at a first energy level. The piezoelectric device comprises a piezoelectric crystal 39, for instance. Two electrodes 40 and 41 sandwich the piezoelectric crystal 39. The piezoelectric crystal 39 has a surface on which bubbles nucleate as described concerning FIG. 1. A solution (not shown) containing an analyte covers the sound source 38. Sound is transmitted by the sound source 38 at a first level. An enzyme/substrate combination causes molecules of a material to be produced, which on the surface of the piezoelectric crystal 39 nucleate as bubbles in response to the concentration of an analyte in the solution covering the piezoelectric crystal 39. Bubbles nucleate on the surface of the piezoelectric crystal 39 and displace molecules of solution from the piezoelectric crystal 39. The displacement of solution molecules directly affects the acoustic energy of the sound source 38, which changes the acoustic impedance of the sound source from a first level to a second level. A resulting decrease in the area of the piezoelectric crystal 39 that interfaces with the solution causes a change in acoustic energy transmission. Thus, sound intensity changes as more bubbles nucleate.

In this embodiment, the displacement of solution from the piezoelectric crystal 39 by the nucleated gas bubbles changes the acoustic impedance of the piezoelectric crystal solution interface. The nucleated gas bubbles displace molecules of the liquid solution containing the analyte from the surface of the piezoelectric crystal 39.

Figure 13:
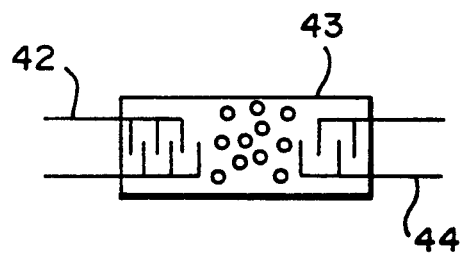
FIG. 13 shows an acoustic embodiment comprising a surface acoustic wave device.

FIG. 13 shows another acoustical embodiment of this invention. A sound source 42 produces acoustical energy at a relatively constant level. A wave surface 43 carries the acoustic energy to an acoustic receiver 44. An enzyme/substrate causes molecules of a material to be produced, which on the wave surface 43 nucleate as bubbles in response to the concentration of an analyte in solution (not shown) covering the wave surface 43. The nucleated bubbles displace molecules of the solution from the wave surface 43. The displacement of solution molecules directly effects the acoustic impedance of the wave surface 43. Energy transmitted by the wave surface 43 changes from a first level to a second level in response to the presence or absence of nucleated bubbles on the wave surface 43.

Figure 14:
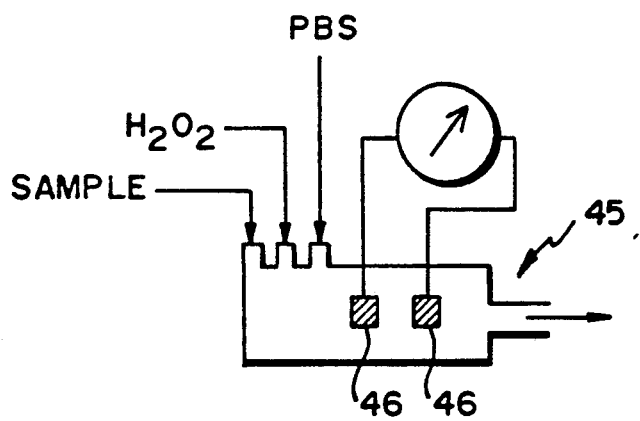
FIG. 14 shows an analysis cell for using an array of sensors.

FIG. 14 shows an analysis cell 45 with an array of sensors 46. Each sensor of the array of sensors 46, comprises a sensor as shown in FIGS. 2-13, for instance. Each sensor 46 has a specific enzyme/substrate combination on a surface of a sensor to test for a particular substance in a solution under test in the container 47. In this manner, multiple measurements can be made simultaneously.

Figure 15:
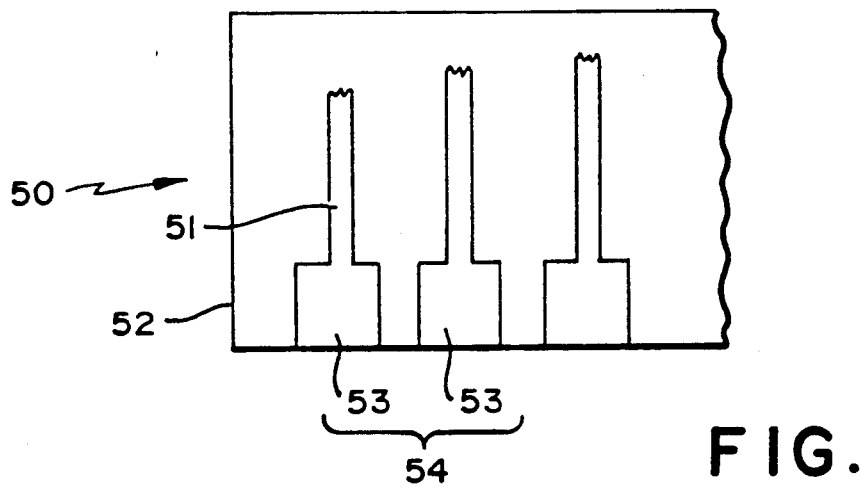
FIG. 15 shows a top view of a structure for supporting a biochemical sensor.

FIG. 15 shows a top view of a support 50 for a biochemical sensor according to this invention. Traces 51 are deposited on a printed circuit board 52. Gold plated trace 51 terminates in a pad 53 on the printed circuit board 52. The surface of the printed circuit board 52 is covered by an insulating material (not shown), such as an epoxy or a plastic laminate, excluding windows that expose each pad 53. A pair of exposed pads constitutes two electrodes of one sensor 54. A multiplicity of sensors 54 can be provided on one printed circuit board 52. The pads 53 comprising exposed gold electrodes are then coated with a thin layer of polymer such as poly(-dimethyl)siloxane, or aminobutylsiloxane, to produce a bubble nucleating surface. To improve nucleation of bubbles, the surface of the pads 53 can be covered with a thin mesh (not shown). When bubbles nucleate on the surface of the pads 53 comprising the polymer-covered electrodes, electrolyte is displaced and resistance between a pair of electrodes increases. Thus energy changes from a first level to a second level.

Figure 16:
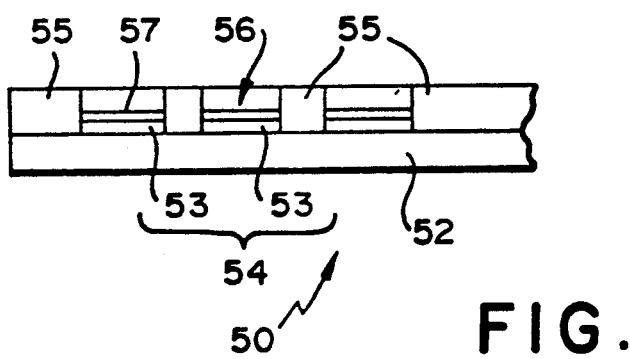
FIG. 16 shows a front view of the structure of FIG. 15.

FIG. 16 is a front view of the structure of FIG. 15. Insulating material 55 sits atop the printed circuit board 52 and windows 56 expose the pads 53 to a test solution. Each pad 53 is covered with a thin layer of polymer 57.

According to this invention, electrical conductors, optical fibers, or acoustic media, for example, comprise surfaces for supporting a biochemical sensor responsive to bubbles. The conductivity, refraction, or propagation, respectively, changes at the surface from a first level to a second level according to the presence of analyte in a solution covering the sensor.

I claim:

1. Apparatus for sensing a biochemical analyte comprising:

a sensor element having surface means which nucleate bubbles from volatile material;

prǒducing means for producing a volatile material in an amount dependent on a concentration of the biochemical analyte in an electrolyte solution, said producing means including an enzyme and having a portion bound to the surface means, said producing means disposed adjacent to the surface means; and detection means having an energy providing means for providing energy and a reception means positioned to receive energy from said energy providing means, said surface means positioned such that bubbles formed thereon in response to presence of the biochemical analyte change energy passing from said energy providing means to said reception means.

2. The apparatus of claim 1, wherein said energy providing means is constructed so as to provide electrical energy to said reception means.

3. The apparatus of claim 2, wherein said energy providing means is separated from said reception means such that the electrolyte solution which is to be tested for presence of the biochemical analyte is disposed between said energy providing means and said reception means.

4. The apparatus of claim 3, wherein said energy providing means is an electrode.

5. The apparatus of claim 4, wherein said electrode is a sintered tantalum pellet through which the electrolyte solution passes.

6. The apparatus of claim 3, wherein said energy providing means is a first electrode and said reception means is a second electrode, and further comprising a filter disposed between said first and second electrodes, said surface means being disposed on said filter.

7. The apparatus of claim 1, wherein said detection means comprises a solid state electronic device having a gate and wherein said surface means is on said gate.

8. The apparatus of claim 1, wherein said energy providing means is constructed so as to provide light energy for reception by said reception means.

9. The apparatus of claim 8, wherein said reception means is a photo-detector.

10. The apparatus of claim 8, further comprising an optical fiber disposed for light passage from said energy providing means to said reception means, said surface means mounted on said optical fiber.

11. The apparatus of claim 8, wherein said surface means is disposed on a mirror.

12. The apparatus of claim 1, wherein said energy providing means is an acoustic source and said reception means receives acoustic energy from said acoustic source.

13. The apparatus of claim 12, wherein said acoustic source is a piezoelectric crystal, and said piezoelectric crystal and reception means define a surface acoustic wave device.

14. The apparatus of claim 8, wherein said enzyme is such as to produce fluorescence when combined with a fluorescing substrate in the electrolyte solution.

* * * * *